US005492124A

United States Patent [19]
Purdy

[11] Patent Number: 5,492,124
[45] Date of Patent: Feb. 20, 1996

[54] METHOD AND APPARATUS FOR IMPROVED MR ANGIOGRAPHY FOR USE IN REGIONS WHERE BLOODFLOW IS REGURGITATED

[75] Inventor: David E. Purdy, East Windsor, N.J.

[73] Assignee: Siemens Medical Systems, Inc., Iselin, N.J.

[21] Appl. No.: 217,297

[22] Filed: Mar. 23, 1994

[51] Int. Cl.$^6$ .......................... A61B 5/0205; A61B 5/055
[52] U.S. Cl. ..................... 128/653.3; 128/653.2; 128/696; 128/708
[58] Field of Search .......................... 128/653.2, 653.3, 128/696, 708; 324/307, 309, 313, 306; 364/413.13

[56] References Cited

U.S. PATENT DOCUMENTS 5,320,099  6/1994  Roberts et al. ..................... 128/653.3

Primary Examiner—Donald E. McElheny, Jr.
Assistant Examiner—Stephen R. Tkacs
Attorney, Agent, or Firm—Mark H. Jay

[57] ABSTRACT

MR angiography method and apparatus either moves the saturation slab or eliminates it during a predetermined portion of the patient's cardiac cycle. This permits an MR image of a slice of interest to contain information relating to arterial bloodflow without becoming degraded by regurgitated bloodflow and information relating to venous bloodflow.

3 Claims, 6 Drawing Sheets

METHOD AND APPARATUS FOR IMPROVED MR ANGIOGRAPHY FOR USE IN REGIONS WHERE BLOODFLOW IS REGURGITATED

BACKGROUND OF THE INVENTION

The invention relates to magnetic resonance (MR) imaging, and more particularly relates to MR angiography. In its most immediate sense, the invention relates to MR angiography of the legs or any other regions wherein bloodflow is regurgitated during the patient's cardiac cycle.

In conventional MR angiography of the arteries, a radiologist seeks to image a slice of interest in such a manner that arterial bloodflow contributes to the image while venous bloodflow does not. This has been done by saturating a slab of the patient immediately adjacent, and arterially downstream of, the slice of interest. The slab so established is known as a "saturation slab".

Saturated blood does not contribute to an MR image. Because the saturation slab is upstream of the slice of interest in the direction of venous bloodflow, venous blood passes through the saturation slab before it enters the slice of interest. Thus, venous bloodflow is 0 saturated by the time it enters the slice of interest and does not contribute to the MR image of the slice of interest. Because the saturation slab is downstream of the slice of interest in the direction of arterial bloodflow, arterial blood in the slice of interest has not previously passed through the saturation slab and therefore is not saturated. As a result, arterial blood contributes to the MR image of the slice of interest. In this way, the MR image of the slice of interest shows arterial bloodflow without venous bloodflow.

However, this technique has a disadvantage when it is used in regions where arterial bloodflow is regurgitated (reversed in direction). For example, let it be assumed that this known technique is used to conduct an MR angiography study of the arteries in a patient's legs, where arterial bloodflow is regurgitated during the patient's cardiac cycle. In this instance, arterial blood will flow into the saturation slab after leaving the slice of interest and will become saturated. During regurgitation, this saturated arterial blood will be withdrawn back into the slice of interest, where it will make no contribution to the MR image. As a result, the MR image of the slice of interest will be degraded.

It would be advantageous to provide method and apparatus which would not produce degraded MR angiographic images when used in locations where arterial blood is regurgitated.

It is, accordingly, one object of the invention to provide method and apparatus for producing an MR angiographic image of a slice of interest in a living patient in such a manner that the MR image is not degraded by regurgitated bloodflow.

Another object is, in general, to improve on known MR methods and apparatus of this general type.

In accordance with the invention, the saturation slab is either moved or eliminated during a single MR sequence. Advantageously, and in accordance with the preferred embodiments, the motion is carried out as a function of the cardiac cycle, or the saturation slab is eliminated, before the regurgitated bloodflow takes place.

By so moving the saturation slab, or by so eliminating it, the regurgitated blood is not saturated and therefore contributes to the image of the slice of interest when such regurgitated blood re-enters the slice of interest.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

The drawings below described have been simplified for simplicity and are not to scale. In all Figures, the same element is always indicated using the same reference number.

Figure 1:
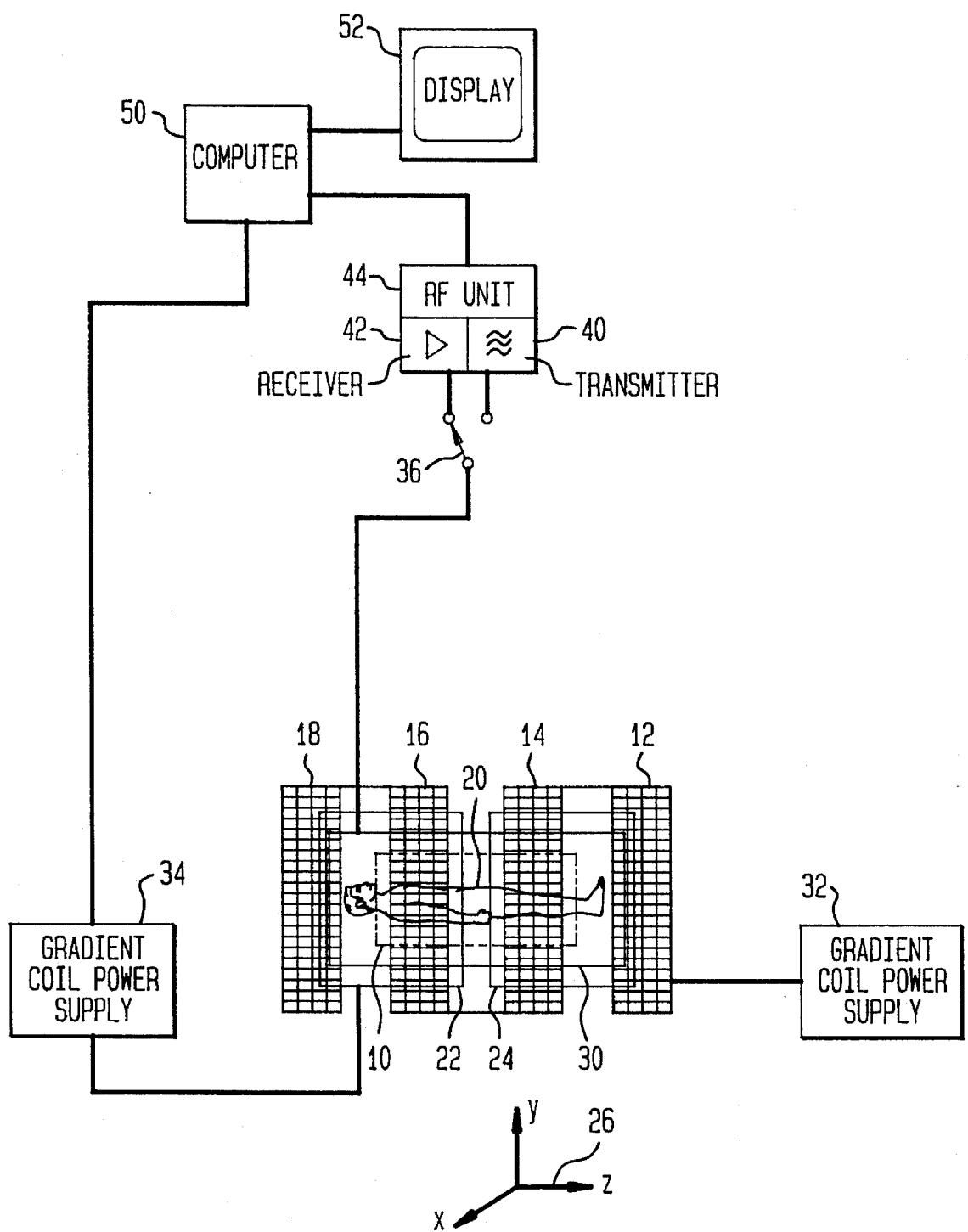
FIG. 1 shows a conventional MR apparatus.

A conventional MR system such as that shown in FIG. 1 has main field coils 12, 14, 16 and 18 which are used to establish the main field in which the patient 20 is placed. Gradient coils 22 and 24, together with other like coils on the other side of the patient, establish a gradient magnetic field along the X direction of the coordinate system 26 of the MR system. Other gradient coils (not shown) establish a gradient magnetic field along the Y direction. An RF coil 30 is used for transmit and receive functions. The radical frequency (RF) coil 30 delivers RF signals to the patient 20 within the examination region 10 and thereby induces resonance of e.g. hydrogen nuclei in the patient 20 which are within the slice of interest. This causes the production of magnetic resonance signals from such hydrogen nuclei; the magnetic resonance signals are picked up by the RF coil 30 and computer-processed to form an image of the slice of interest.

The main field coils 12, 14, 16 and 18 are energized by a main coil power supply 32, and the gradient coils (including the coils 22 and 24 but not limited to them) are energized by a gradient coil power supply 34. The gradient coil power supply 34 is in turn controlled by a computer 50.

In use, the computer 50 causes RF pulses to be produced by the RF unit 44. The pulses are then routed through a transmitter 40 and a switch 36 to the RF coil 30. This induces the MR effect in e.g. hydrogen nuclei within the patient 20. Then, the switch 36 is thrown to its other position, MR resonance signals from the patient 20 are picked up by the RF coil 30, received via the receiver 42 and routed to the computer 50 via the RF unit 44. The computer 50 is then used to reconstruct MR images of the slice of interest, and these reconstructed MR images can be output to a display 52 or other output device.

In conventional MR angiography, the MR signal from a sample in a region of space may be substantially reduced by "saturating" that region. Before such saturation, the nuclear spins in the sample within the region have a net magnetization along the Z direction. To saturate the sample within the region, an RF pre-pulse and one or more gradient pulses are applied to the RF and gradient coils respectively. This nutates, or flips, the spins of the nuclei within the desired slab of the sample towards the X-Y plane, thereby eliminating the net magnetization along the Z direction, orienting the nuclear spins variously within the X-Y plane ("dephasing" the nuclear spins) and consequently preventing the nuclei with nutated spins from producing an MR signal. In this state, the nuclei are "saturated", and the region in which this saturation exists is known as the "saturation slab".

Although the saturated nuclei gradually regain the ability to produce an MR signal as natural relaxation processes cause the nuclei to regain a net magnetization along the Z direction, this process is a function of time alone and it occurs relatively slowly for hydrogen nuclei in the blood. As a result, the saturated nuclei produce no MR signal until long after the interval in which MR signals from the predetermined desired slice are picked up by the RF coil 30, routed to the computer 50, and used to construct MR images.

It may thus be understood that nuclei within the saturation slab during the RF pre-pulse and gradient pulse(s) do not produce an MR signal during the window of time when the MR system "looks" for such a signal. As a result, even if such saturated nuclei are physically moved (as is the case with hydrogen nuclei in the blood, which nuclei move as the blood flows through the circulatory system) they do not contribute to any MR images.

Figure 2A:
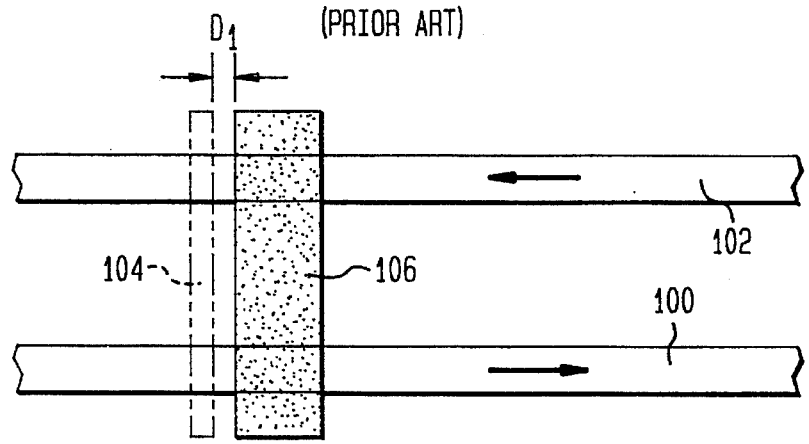
FIGS. 2A, 2B and 2C show a conventional method used in MR angiography and the consequences of arterial regurgitation when that method is used.
Figure 2B:
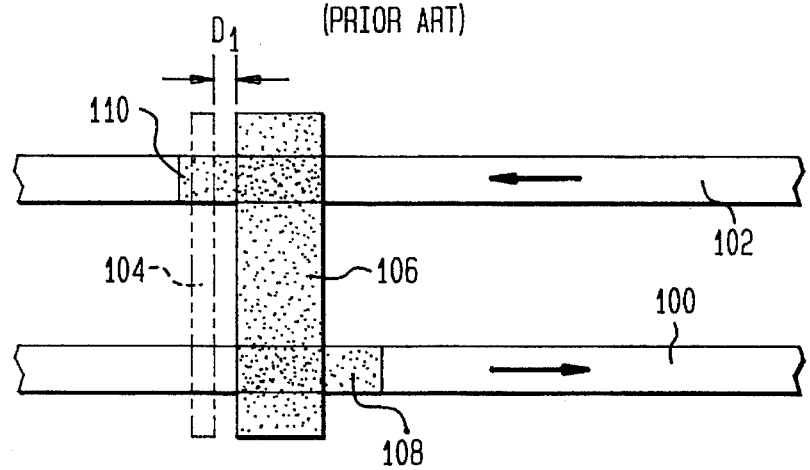

A conventional MR angiography study will now be described in connection with FIGS. 2A and 2B. FIGS. 2A and 2B are schematic, and not to scale.

An artery 100 and a vein 102 pass through a slice of interest 104 in a patient (not otherwise shown). Although the artery 100 and the vein 102 are shown as widely spaced apart from each other, this is often not so; in the human body, arteries and veins are frequently close together. Since a diagnostician often wishes to identify e.g. a stenosis in an artery, diagnosticians do not want the MR image of arterial bloodflow to be obscured or degraded by the MR image of immediately adjacent venous bloodflow. Therefore, diagnosticians often wish to obtain an MR image of the slice of interest 104 which includes the image of blood that flows through the artery 100 and which excludes the image of blood that flows through the vein 102. (It is alternatively possible to image the slice of interest with venous blood and without arterial blood, but the present discussion will focus upon arterial bloodflow because venous bloodflow is not regurgitated—see below.)

To obtain such an image, a saturation slab 106 is established immediately adjacent, and arterially downstream of, the slice of interest 104. (As shown, this saturation slab 106 is not to scale; it is thicker than the slice of interest 104, but the thickness depends upon the rate of bloodflow into the slice of interest, and is not a part of the invention.) $D_1$ indicates the distance between the slice of interest 104 and the saturation slab 106; a positive value of $D_1$ indicates a gap between the slice of interest 104 and the saturation slab 106, while a negative value of $D_1$ indicates an overlap between the slice of interest 104 and the saturation slab.

Blood flowing through the artery 100 to the right as viewed in FIG. 2B contributes to the MR image of the slice of interest 104. This is because the hydrogen nuclei in this blood do not become saturated until after they have exited the slice of interest 104; region 108, which contains saturated blood, is downstream of the saturation slab 106. However, blood flowing through the vein 102 to the left as viewed in FIG. 2A does not contribute to the MR image of the slice of interest 104. This is because the nuclei in region 110 of the venous bloodflow are saturated in the saturation slab 106 and do not produce an MR signal while they are located within the slice of interest 104. Blood in region 110 consequently does not contribute to an MR image of the slice of interest 104. As a result, the MR image of the slice of interest 104 reflects only arterial bloodflow and not venous bloodflow.

Figure 2C:
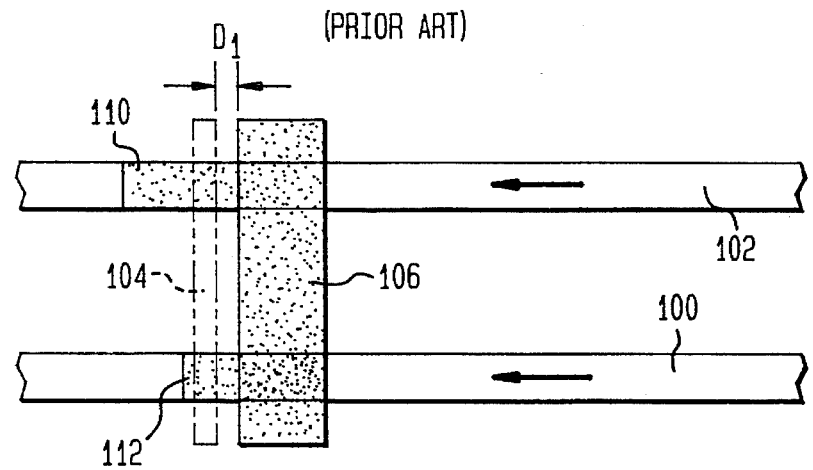

Let it now be assumed that an MR angiography study is to be conducted of e.g. the patient's legs. While venous bloodflow is ordinarily unidirectional, and can be imaged using conventional techniques described above, arterial bloodflow in the leg arteries (e.g. the iliac, femoral, popliteal and tibial arteries) as well as certain other arteries is not unidirectional. This is because certain arterial walls are elastic and can act like balloons which expand during certain parts of the cardiac cycle and which contract at other parts of the cardiac cycle. Thus, at a particular time during the patient's cardiac cycle, the walls of the artery of interest may contract, causing the arterial bloodflow to be regurgitated, i.e. reversed within the arteries. The consequences of this will now be explained in connection with FIG. 2C.

A volume 112 of arterial bloodflow, which has previously flowed through the slice of interest 104, enters the saturation slab 106 in the first part of the patient's cardiac cycle. While the hydrogen nuclei in the volume 112 of arterial blood are located in the saturation slab 106, these nuclei become saturated by the RF pre-pulse and gradient pulse(s) and do not thereafter contribute to any MR image acquired during the relevant time frame. When, during regurgitation of the arterial bloodflow, a saturated portion of the volume 112 of arterial blood re-enters the slice of interest 104, that saturated portion of the regurgitated blood cannot contribute to the MR image of the slice of interest 104. As a consequence, the MR image of the slice of interest 104 is degraded.

Figure 3:
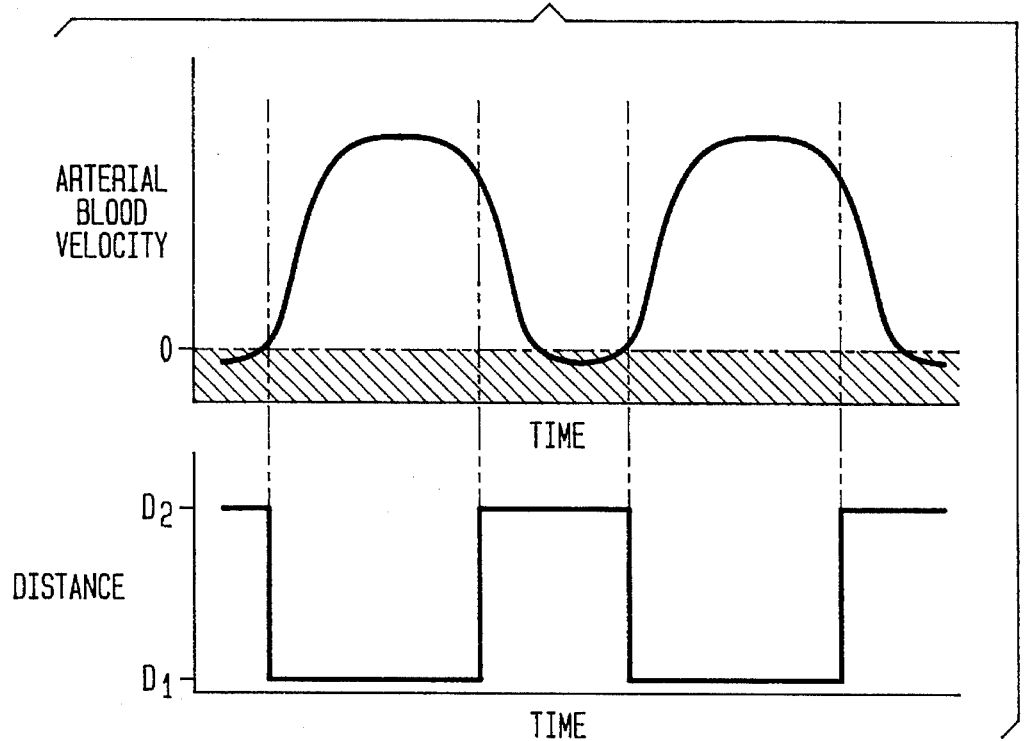
FIG. 3 shows a method in accordance with a first preferred embodiment of the invention.

In accordance with a first preferred embodiment of the invention, the location of the saturation slab 106 is changed during a single sequence in accordance with the patient's cardiac cycle, as can be seen in FIG. 3. After the maximum rate of arterial bloodflow has commenced, the saturation slab 106 is moved arterially downstream from its initial location to a larger distance $D_2$ away from the slice of interest 104. Thereafter, and before commencement of regurgitated arterial bloodflow, movement of the saturation slab 106 ceases. After regurgitated arterial bloodflow has ceased, the saturation slab 106 is relocated to its initial position at a distance $D_1$ from the slice of interest 104.

Figure 4A:
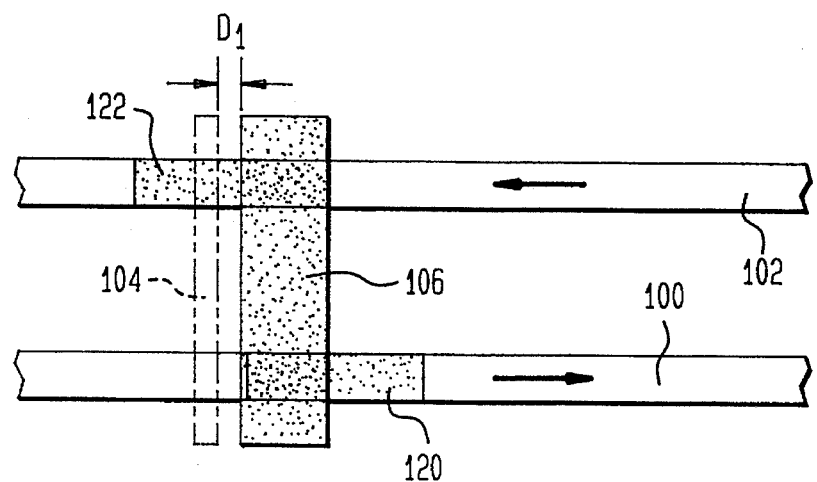
FIGS. 4A, 4B, 4C and 4D show the operation of a method in accordance with the first preferred embodiment of the invention.

The operation of this first preferred embodiment will now be explained in accordance with FIGS. 4A, 4B and 4C. Initially, and as is shown in FIG. 4A, the saturation slab 106 is located a distance $D_1$ downstream from the slice of interest 104 along the direction of arterial bloodflow. Arterial blood within the saturation slab 106 is saturated, and arterial blood within arterial region 120 is saturated from previous application of the saturating RF pre-pulse and gradient pulse(s). These saturations have no effect on arterial blood upstream of the saturation slab 106 and the MR image of the slice of interest 104 includes a contribution from this unaffected upstream arterial blood. Venous blood within the saturation slab 106 and (from prior saturation pulses) within venous region 122 is saturated, and does not contribute to the MR image of the slice of interest 104 since the nuclei within such venous blood do not produce a MR signal while they are within the slice of interest 104.

Figure 4B:
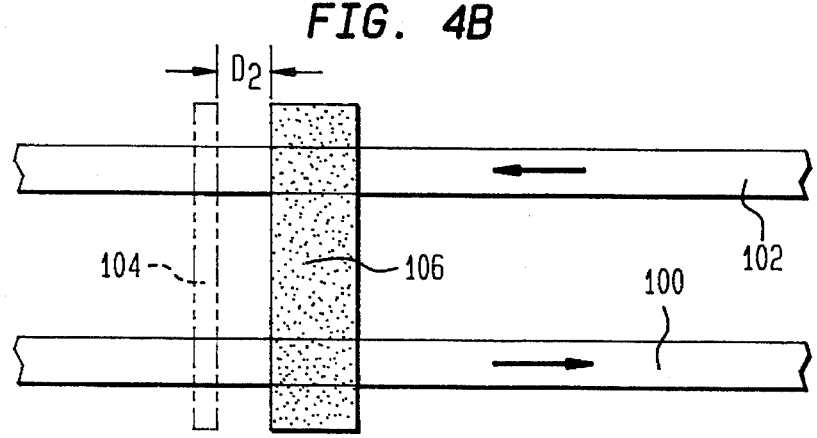
Figure 4C:
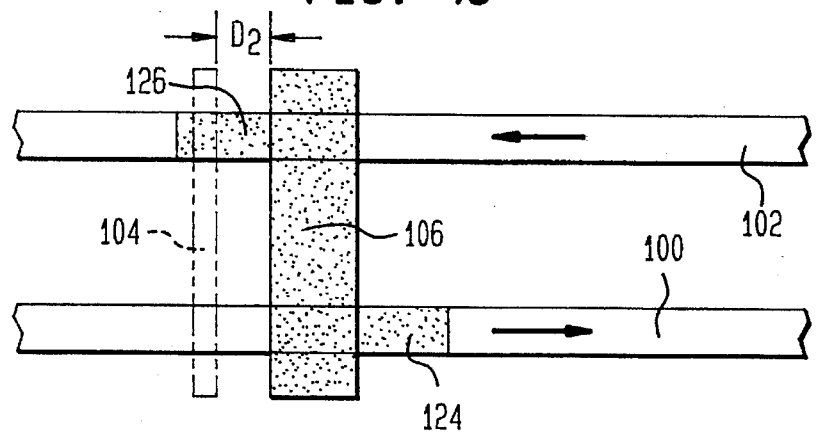

After the patient's cardiac cycle has advanced to the stage where maximum arterial blood velocity has been reached, the saturation slab 106 is moved arterially downstream from the slice of interest 104 to a new distance $D_2$, as is illustrated in FIG. 4B. Blood continues to flow through the artery 100 and the vein 102, causing arterial blood in region 124 and venous blood in region 126 to be saturated as the blood passes through the saturation slab 106 (see FIG. 4C). Unsaturated arterial blood fills the gap $D_2$ between the slice of interest 104 and the new position of the saturation slab 106 as shown in FIG. 4C.

Figure 4D:
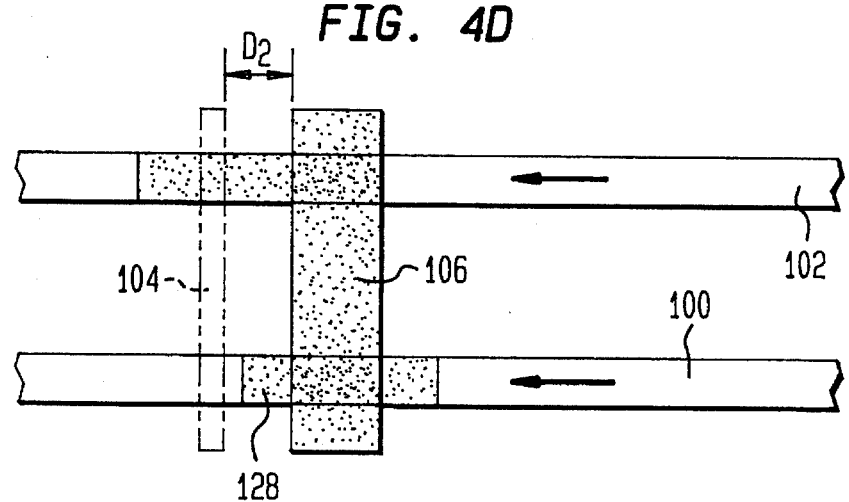

Once regurgitation takes place, as is illustrated in FIG. 4D, arterial bloodflow is reversed and blood which was saturated in the saturation slab 106 flows back into region 128 towards the slice of interest 104. However, the thus-saturated regurgitated arterial blood does not flow into the slice of interest 104 because the regurgitation does not continue long enough for this to happen. As a result, the saturated regurgitated arterial blood does not degrade the MR image of the slice of interest 104 because this saturated blood never enters the slice of interest 104.

After regurgitation has ended, the saturation slab 106 is restored to its original position at a distance $D_1$ from the slice of interest 104 and the cycle is repeated once more.

A second preferred embodiment of the invention differs from the first preferred embodiment in that instead of moving the saturation slab 106, the saturation slab 106 is eliminated.

Figure 5:
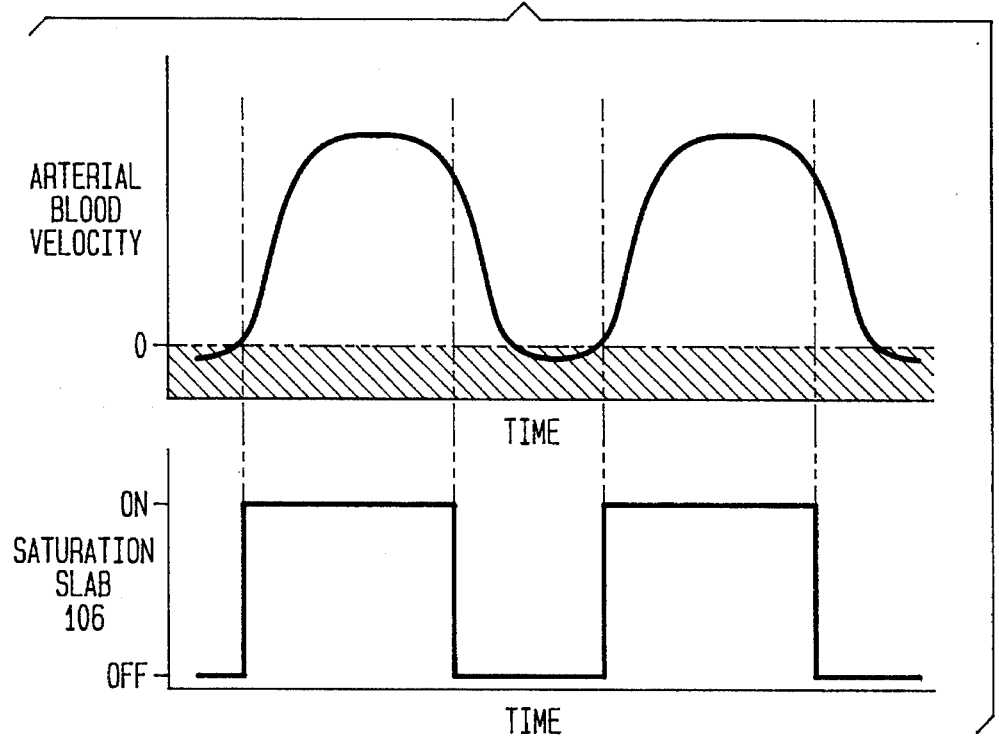
FIG. 5 shows a method in accordance with a second preferred embodiment of the invention.

With reference to FIG. 5, in accordance with the second preferred embodiment of the invention, the saturation slab 106 is turned on and is located at the distance $D_3$ away from the slice of interest 104. After the arterial blood velocity has reached its maximum value, the saturation slab 106 is eliminated until regurgitated bloodflow has commenced and concluded. Thereafter, the saturation slab 106 is turned on again and the cycle is repeated.

Figure 6A:
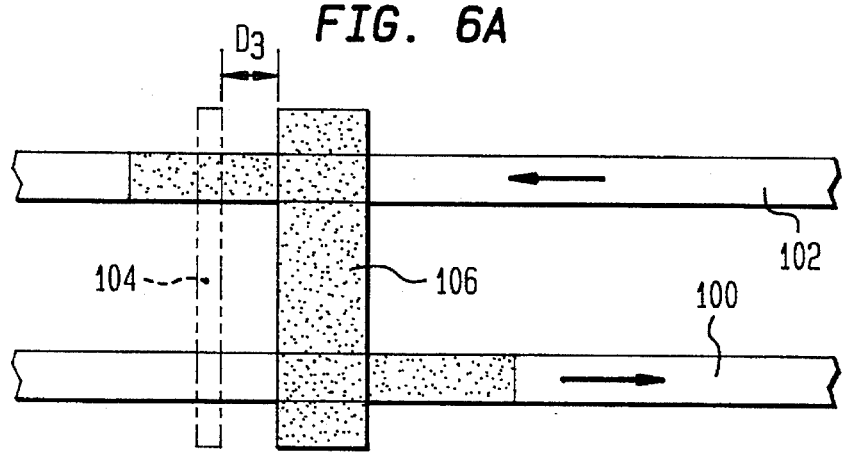
FIGS. 6A and 6B show the operation of a method in accordance with the second preferred embodiment of the invention.
Figure 6B:
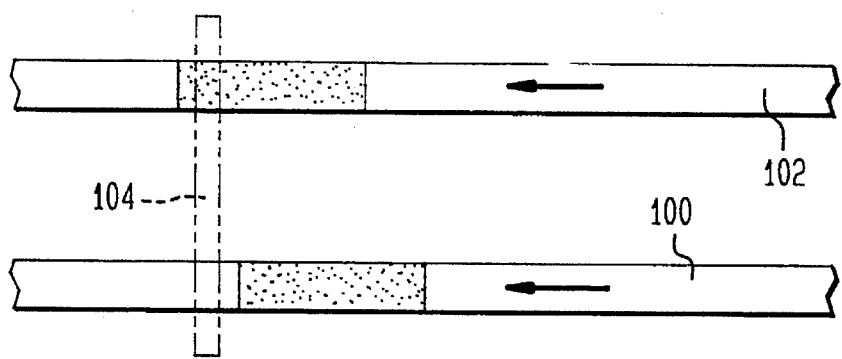

In accordance with the second preferred embodiment of the invention as illustrated in FIG. 6A, the saturation slab 106 is separated from the slice of interest 104 by a distance $D_3$ until after maximum arterial blood velocity has been reached. Then, as is illustrated in FIG. 6B, the saturation slab 106 is turned off. Because of this, further saturation of blood does not take place. The distance $D_3$ is so chosen that regurgitated blood will not reach the slice of interest 104 by the time that data from the slice of interest 104 is accumulated.

There is no requirement that distances $D_1$ and $D_3$ be the same or that they differ from each other.

Figure 7:
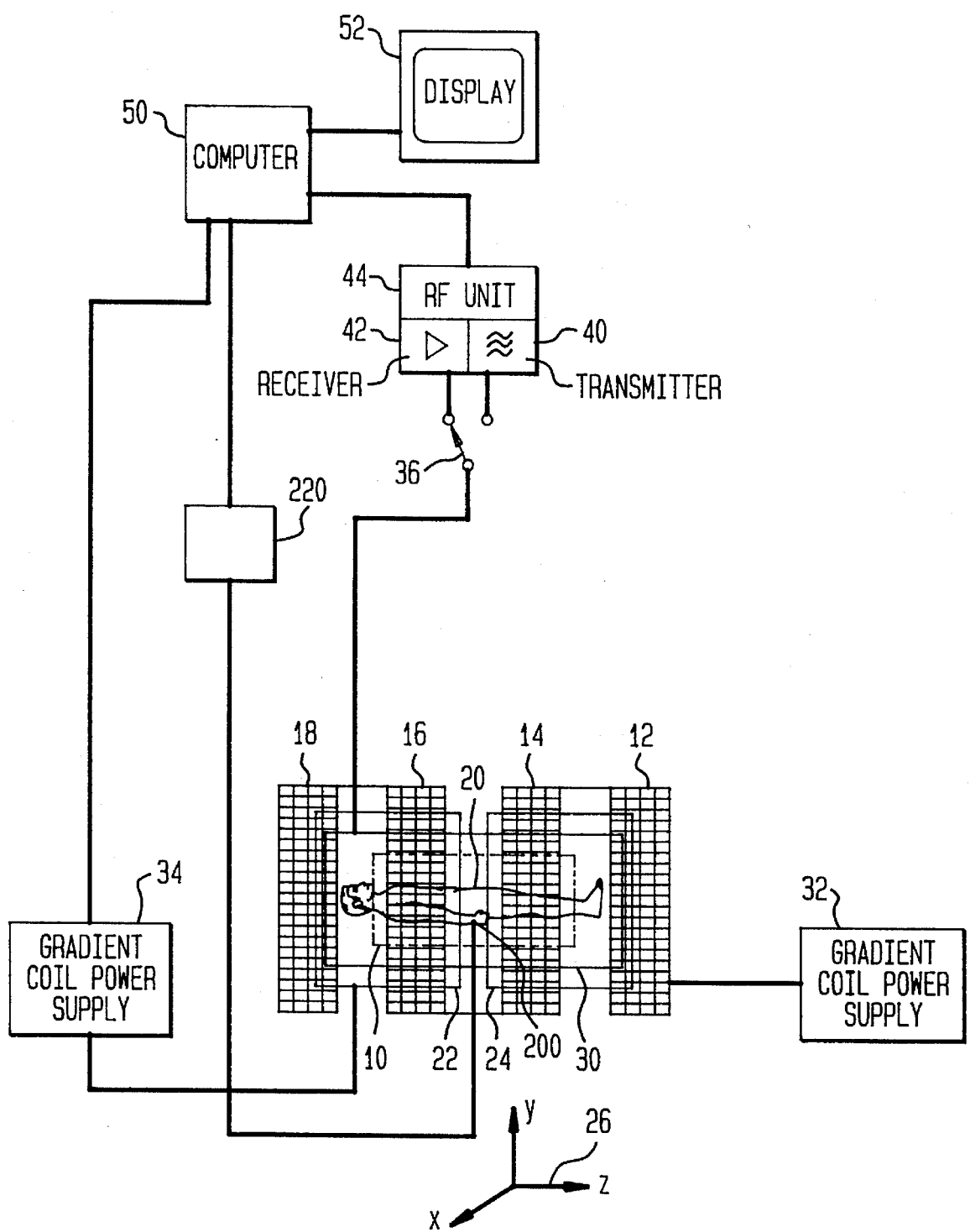
FIG. 7 shows apparatus in accordance with a preferred embodiment of the invention.

Advantageously, the establishment, elimination, or movement of the saturation slab 106 may be carried out without specific input from the technician. This may be done by monitoring the patient's cardiac cycle and triggering the MR system in accordance therewith. Cardiac monitoring may (see FIG. 7) advantageously be carried out by connecting electrodes 200 to the patient and by using electrical circuitry 220 to analyze the patient's cardiac cycle and to output trigger signals to the computer 50 at appropriate times during the cardiac cycle.

Although a preferred embodiment has been described above, the scope of the invention is limited only by the following claims:

I claim:

1. Apparatus for producing an MR angiographic image of a slice of interest in a living patient in such a manner that the image is not degraded by regurgitated bloodflow, comprising:

means for establishing a saturation slab adjacent the slice of interest;

means for monitoring the patient's cardiac cycle;

means for eliminating said slab for a predetermined period of time after maximum unregurgitated bloodflow rate has commenced; and means restoring said slab to its original position adjacent the slice of interest after regurgitated bloodflow has ceased.

2. A method for producing an MR angiographic image of a slice of interest in a living patient in such a manner that the image is not degraded by regurgitated bloodflow, comprising the following steps:

establishing a saturation slab adjacent the slice of interest;

monitoring the patient's cardiac cycle;

eliminating said slab for a predetermined period of time after maximum unregurgitated bloodflow rate has commenced;

restoring said slab to its original position adjacent the slice of interest after regurgitated bloodflow has ceased; and producing an MR angiographic image of the slice of interest.

3. A method for producing an MR angiographic image of a slice of interest in a living patient in such a manner that the image is not degraded by regurgitated bloodflow, comprising the following steps:

establishing a saturation slab adjacent the slice of interest;

monitoring the patient's cardiac cycle;

moving, as a function of the patient's cardiac cycle, the saturation slab with respect to the slice of interest, said moving step comprising the steps of moving said slab along the direction of unregurgitated bloodflow after maximum unregurgitated bloodflow rate has commenced, ceasing movement of said slab prior to commencement of regurgitated bloodflow, and restoring said slab to its original position adjacent the slice of interest after regurgitated bloodflow has ceased; and forming an MR angiographic image of the slice of interest.

* * * * *